(12) United States Patent
Tykocinski et al.

(10) Patent No.: US 10,533,054 B2
(45) Date of Patent: Jan. 14, 2020

(54) AGONIST FUSION PROTEIN FOR CD40 AND OX40 AND METHODS OF STIMULATING THE IMMUNE SYSTEM

(71) Applicant: THOMAS JEFFERSON UNIVERSITY, Philadelphia, PA (US)

(72) Inventors: Mark L. Tykocinski, Merion Station, PA (US); Matthew Charles Weber, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 551 days.

(21) Appl. No.: 14/763,730

(22) PCT Filed: Jan. 31, 2014

(86) PCT No.: PCT/US2014/014200
§ 371 (c)(1),
(2) Date: Jul. 27, 2015

(87) PCT Pub. No.: WO2014/121099
PCT Pub. Date: Aug. 7, 2014

(65) Prior Publication Data
US 2015/0368350 A1 Dec. 24, 2015

Related U.S. Application Data

(60) Provisional application No. 61/759,326, filed on Jan. 31, 2013.

(51) Int. Cl.
*C07K 16/28* (2006.01)
*A61K 39/395* (2006.01)
*C07K 14/705* (2006.01)

(52) U.S. Cl.
CPC ...... *C07K 16/2878* (2013.01); *A61K 39/3955* (2013.01); *C07K 14/70575* (2013.01); *C07K 2317/622* (2013.01); *C07K 2317/75* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,242,687 A | 9/1993 | Tykocinski et al. |
| 5,601,828 A | 2/1997 | Tykocinski et al. |
| 5,623,056 A | 4/1997 | Tykocinski et al. |
| 6,316,256 B1 | 11/2001 | Tykocinski et al. |
| 6,420,172 B1 | 7/2002 | Tykocinski et al. |
| 6,797,489 B2 | 9/2004 | Tykocinski et al. |
| 7,435,585 B2 | 10/2008 | Tykocinski et al. |
| 7,550,140 B2 | 6/2009 | Bakker et al. |
| 7,569,663 B2 | 8/2009 | Tykocinski et al. |
| 7,959,925 B2 | 6/2011 | Weinberg et al. |
| 8,039,437 B2 | 10/2011 | Tykocinski et al. |
| 8,283,450 B2 | 10/2012 | Kato et al. |
| 8,329,657 B2 | 12/2012 | Tykocinski et al. |
| 9,079,976 B2 | 7/2015 | Shirwan et al. |
| 2004/0197876 A1 | 10/2004 | Tschopp et al. |
| 2009/0081157 A1* | 3/2009 | Kornbluth ............... A61K 39/21 424/85.2 |
| 2010/0136032 A1 | 6/2010 | Weinberg et al. |
| 2010/0239633 A1* | 9/2010 | Strome ................ C07K 16/065 424/423 |
| 2010/0291109 A1* | 11/2010 | Kedl ................... A61K 39/0008 424/173.1 |
| 2010/0303811 A1* | 12/2010 | Ochi ................... A61K 39/0008 424/134.1 |
| 2011/0027276 A1* | 2/2011 | Bernett .............. C07K 16/2878 424/133.1 |
| 2011/0041190 A1 | 2/2011 | Tykocinski et al. |
| 2011/0287009 A1 | 11/2011 | Scheer et al. |
| 2012/0121640 A1 | 5/2012 | Tykocinski |
| 2012/0263732 A1 | 10/2012 | Gladue et al. |

FOREIGN PATENT DOCUMENTS

| | | |
|---|---|---|
| WO | 02090553 A2 | 11/2002 |
| WO | 2011109789 A2 | 9/2011 |
| WO | 2012149356 A2 | 11/2012 |

OTHER PUBLICATIONS

Khong et al., International Reviews of Immunology 31: 246-266 (2012). (Year: 2012).*
Vonderheide et al., Clin Cancer Res. 19: 1035-1043 (2013) (Year: 2013).*
Rudikoff et al., Proc Natl Acad Sci USA 79: 1979-1983 (1982). (Year: 1982).*
Colman, Research in Immunology 145: 33-36 (1994) (Year: 1944).*
Kussie et al., J. Immunol. 152: 146-152 (1994). (Year: 1994).*
Chen et al., EMBO J., 14: 2784-2794 (1995). (Year: 1995).*
Croft, "Control of Immunity by the TNFR-Related Molecule OX40 (CD134)", Annual Review of Immunology. 28(1), Mar. 2010, 57-78.
Loskog, et al., "CD40L—A multipotent molecule for tumor therapy", Endocrine, Metabolic, & Immune Disorders—Drug Targets, Bentham Science Publishers Ltd., Bussum NL, 7(1), Mar. 2007, 23-28.
Supplementary European Search Report for European Patent Application No. 14745477.1 dated May 24, 2016.
The International Search Report and the Written Opinion of the International Searching Authority (Apr. 25, 2014).
Biagi et al,"Molecular transfer of CD40 and OX40 ligands to leukemic human B cells induces expansion of autologous tumor-reactive cytotoxic T lymphocytes," Blood, 105(6): 2436-2442 (Mar. 15, 2005).
Liu et al, "The adjuvancy of OX40 ligand (CD252) on an HIV-1 canarypox vaccine," Vaccine, 27: 5077-5084 (2009).
Mazzei et al, "Recombinant Soluble Trimeric CD40 Ligand Is Biologically Active," The Journal of Biological Chemistry, 270(13): 7025-7028 (1995).
Karpusas et al, "Structure of CD40 Ligand in Complex with the Fab Fragment of a Neutralizing Humanized Antibody," Structure, 9: 321-329 (Apr. 2001).

(Continued)

*Primary Examiner* — Phillip Gambel
(74) *Attorney, Agent, or Firm* — Saul Ewing Arnstein & Lehr LLP; Kathryn Doyle; Jacque C. Young

(57) ABSTRACT

Provided is a fusion protein comprising an agonist for CD40 and an agonist for OX40. Compositions comprising the fusion protein and methods of use are also provided.

13 Claims, 2 Drawing Sheets

Specification includes a Sequence Listing.

(56) References Cited

OTHER PUBLICATIONS

Van Kooten et al, "CD40-CD40 ligand," Journal of Leukocyte Biology, 67: 2-17 (Jan. 2000).
Clark et al, "Activation of human B cells mediated through two distinct cell surface differentiation antigens, Bp35 and Bp50," Proc. Natl. Acad. Sci. USA, 83: 4494-4498 (Jun. 1986).
Francisco et al, "Activity of a Single-Chain Immunotoxin That Selectively Kills Lymphoma and Other B-Lineage Cells Expressing the CD40 Antigen," Cancer Research, 55: 3099-3104 (Jul. 15, 1995).
Gladue et al, "The CD40 agonist antibody CP-870,893 enhances dendritic cell and B-cell activity and promotes anti-tumor efficacy in SCID-hu mice," Cancer Immunol Immunother, DOI 10.1007/s00262-011-1014-6 (Apr. 12, 2011).

\* cited by examiner

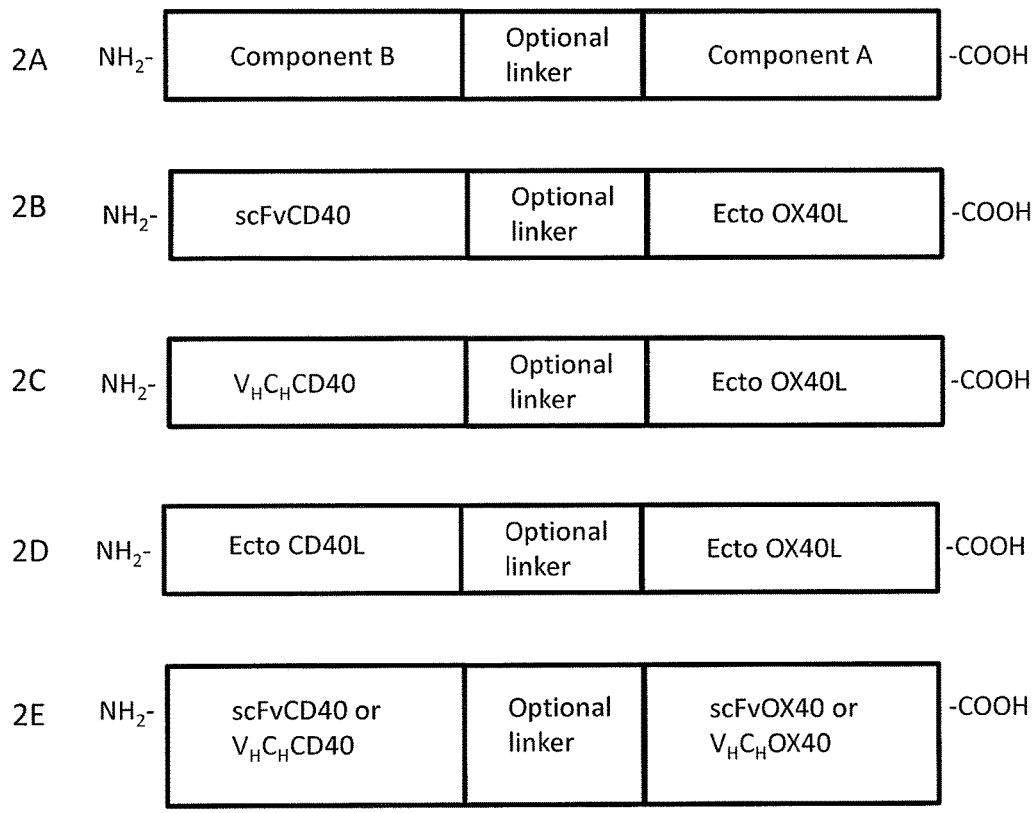

SEQUENCE LISTING

<160> NUMBER OF SEQ ID NOS: 18

<210> SEQ ID NO 1
<211> LENGTH: 178
<212> TYPE: PRT
<213> ORGANISM: Homo sapiens

<400> SEQUENCE: 1

Val Thr Gly Leu His Cys Val Gly Asp Thr Tyr Pro Ser Asn Asp Arg
1               5                   10                  15

Cys Cys His Glu Cys Arg Pro Gly Asn Gly Met Val Ser Arg Cys Ser
            20                  25                  30

Arg Ser Gln Asn Thr Val Cys Arg Pro Cys Gly Pro Gly Phe Tyr Asn
        35                  40                  45

Asp Val Val Ser Ser Lys Pro Cys Lys Pro Cys Thr Trp Cys Asn Leu
    50                  55                  60

Arg Ser Gly Ser Glu Arg Lys Gln Leu Cys Thr Ala Thr Gln Asp Thr
65                  70                  75                  80

Val Cys Arg Cys Arg Ala Gly Thr Gln Pro Leu Asp Ser Tyr Lys Pro
                85                  90                  95

Gly Val Asp Cys Ala Pro Cys Pro Pro Gly His Phe Ser Pro Gly Asp
            100                 105                 110

Asn Gln Ala Cys Lys Pro Trp Thr Asn Cys Thr Leu Ala Gly Lys His
        115                 120                 125

Thr Leu Gln Pro Ala Ser Asn Ser Ser Asp Ala Ile Cys Glu Asp Arg
    130                 135                 140

Asp Pro Pro Ala Thr Gln Pro Gln Glu Thr Gln Gly Pro Pro Ala Arg
145                 150                 155                 160

Pro Ile Thr Val Gln Pro Thr Glu Ala Trp Pro Arg Thr Ser Gln Gly
                165                 170                 175

Pro Ser

<210> SEQ ID NO 2
<211> LENGTH: 137
<212> TYPE: PRT
<213> ORGANISM: Homo sapiens

<400> SEQUENCE: 2

Phe Ser Ala Leu Gln Val Ser His Arg Tyr Pro Arg Ile Gln Ser Ile
1               5                   10                  15

Lys Val Gln Phe Thr Glu Tyr Lys Lys Glu Lys Gly Phe Ile Leu Thr
            20                  25                  30

Ser Gln Lys Glu Asp Glu Ile Met Lys Val Gln Asn Asn Ser Val Ile
        35                  40                  45

Ile Asn Cys Asp Gly Phe Tyr Leu Ile Ser Leu Lys Gly Tyr Phe Ser
    50                  55                  60

Gln Glu Val Asn Ile Ser Leu His Tyr Gln Lys Asp Glu Glu Pro Leu
65                  70                  75                  80

Phe Gln Leu Lys Lys Val Arg Ser Val Asn Ser Leu Met Val Ala Ser
                85                  90                  95

Leu Thr Tyr Lys Asp Lys Val Tyr Leu Asn Val Thr Thr Asp Asn Thr
            100                 105                 110

Ser Leu Asp Asp Phe His Val Asn Gly Gly Glu Leu Ile Leu Ile His
            115                 120                 125

Gln Asn Pro Gly Glu Phe Cys Val Leu
            130                 135

<210> SEQ ID NO 3
<211> LENGTH: 127
<212> TYPE: PRT
<213> ORGANISM: Homo sapiens

<400> SEQUENCE: 3

Pro Arg Ile Gln Ser Ile Lys Val Gln Phe Thr Glu Tyr Lys Lys Glu
1               5                   10                  15

Lys Gly Phe Ile Leu Thr Ser Gln Lys Glu Asp Glu Ile Met Lys Val
                20                  25                  30

Gln Asn Asn Ser Val Ile Ile Asn Cys Asp Gly Phe Tyr Leu Ile Ser
            35                  40                  45

Leu Lys Gly Tyr Phe Ser Gln Glu Val Asn Ile Ser Leu His Tyr Gln
        50                  55                  60

Lys Asp Glu Glu Pro Leu Phe Gln Leu Lys Lys Val Arg Ser Val Asn
65                  70                  75                  80

Ser Leu Met Val Ala Ser Leu Thr Tyr Lys Asp Lys Val Tyr Leu Asn
                85                  90                  95

Val Thr Thr Asp Asn Thr Ser Leu Asp Asp Phe His Val Asn Gly Gly
            100                 105                 110

Glu Leu Ile Leu Ile His Gln Asn Pro Gly Glu Phe Cys Val Leu
        115                 120                 125

<210> SEQ ID NO 4
<211> LENGTH: 112
<212> TYPE: PRT
<213> ORGANISM: Mus musculus

<400> SEQUENCE: 4

Asp Ala Val Met Thr Gln Asn Pro Leu Ser Leu Pro Val Ser Leu Gly
1               5                   10                  15

Asp Glu Ala Ser Ile Ser Cys Arg Ser Ser Gln Ser Leu Glu Asn Ser
                20                  25                  30

Asn Gly Asn Thr Phe Leu Asn Trp Phe Phe Gln Lys Pro Gly Gln Ser
            35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Tyr Thr Phe Gly Gly Gly Thr Thr Leu Glu Ile Lys
            100                 105                 110

<210> SEQ ID NO 5
<211> LENGTH: 112
<212> TYPE: PRT
<213> ORGANISM: Mus musculus

<400> SEQUENCE: 5

Asp Ile Gln Leu Gln Gln Ser Gly Pro Gly Leu Val Lys Pro Ser Gln
1               5                   10                  15

Ser Leu Ser Leu Thr Cys Ser Val Thr Gly Tyr Ser Ile Thr Thr Asn
            20                  25                  30

Tyr Asn Trp Asn Trp Ile Arg Gln Phe Pro Gly Asn Lys Leu Glu Trp
        35                  40                  45

Met Gly Tyr Ile Arg Tyr Asp Gly Thr Ser Glu Tyr Thr Pro Ser Leu
    50                  55                  60

Lys Asn Arg Val Ser Ile Thr Arg Asp Thr Ser Met Asn Gln Phe Phe
65                  70                  75                  80

Leu Arg Leu Thr Ser Val Thr Pro Glu Asp Thr Ala Thr Tyr Tyr Cys
                85                  90                  95

Ala Arg Leu Asp Tyr Trp Gly Gln Gly Thr Ser Val Thr Val Ser Ser
            100                 105                 110

<210> SEQ ID NO 6
<211> LENGTH: 171
<212> TYPE: PRT
<213> ORGANISM: Homo sapiens

<400> SEQUENCE: 6

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg
                165                 170

<210> SEQ ID NO 7
<211> LENGTH: 98
<212> TYPE: PRT
<213> ORGANISM: Homo sapiens

<400> SEQUENCE: 7

Cys Arg Glu Lys Gln Tyr Leu Ile Asn Ser Gln Cys Cys Ser Leu Cys

```
                1               5                   10                  15
    Gln Pro Gly Gln Lys Leu Val Ser Asp Cys Thr Glu Phe Thr Glu Thr
                    20                  25                  30

Glu Cys Leu Pro Cys Gly Glu Ser Glu Phe Leu Asp Thr Trp Asn Arg
                    35                  40                  45

Glu Thr His Cys His Gln His Lys Tyr Cys Asp Pro Asn Leu Gly Leu
                50                  55                  60

Arg Val Gln Gln Lys Gly Thr Ser Glu Thr Asp Thr Ile Cys Thr Cys
     65                  70                  75                  80

Glu Glu Gly Trp His Cys Thr Ser Glu Ala Cys Glu Ser Cys Val Leu
                        85                  90                  95

His Arg

<210> SEQ ID NO 8
<211> LENGTH: 217
<212> TYPE: PRT
<213> ORGANISM: Homo sapiens

<400> SEQUENCE: 8

Tyr Leu His Arg Arg Leu Asp Lys Ile Glu Asp Glu Arg Asn Leu His
     1               5                   10                  15

Glu Asp Phe Val Phe Met Lys Thr Ile Gln Arg Cys Asn Thr Gly Glu
                    20                  25                  30

Arg Ser Leu Ser Leu Leu Asn Cys Glu Glu Ile Lys Ser Gln Phe Glu
                    35                  40                  45

Gly Phe Val Lys Asp Ile Met Leu Asn Lys Glu Glu Thr Lys Lys Glu
                50                  55                  60

Asn Ser Phe Glu Met Gln Lys Gly Asp Gln Asn Pro Gln Ile Ala Ala
     65                  70                  75                  80

His Val Ile Ser Glu Ala Ser Ser Lys Thr Thr Ser Val Leu Gln Trp
                        85                  90                  95

Ala Glu Lys Gly Tyr Tyr Thr Met Ser Asn Asn Leu Val Thr Leu Glu
                    100                 105                 110

Asn Gly Lys Gln Leu Thr Val Lys Arg Gln Gly Leu Tyr Tyr Ile Tyr
                    115                 120                 125

Ala Gln Val Thr Phe Cys Ser Asn Arg Glu Ala Ser Ser Gln Ala Pro
                130                 135                 140

Phe Ile Ala Ser Leu Cys Leu Lys Ser Pro Gly Arg Phe Glu Arg Ile
    145                 150                 155                 160

Leu Leu Arg Ala Ala Asn Thr His Ser Ser Ala Lys Pro Cys Gly Gln
                    165                 170                 175

Gln Ser Ile His Leu Gly Gly Val Phe Glu Leu Gln Pro Gly Ala Ser
                        180                 185                 190

Val Phe Val Asn Val Thr Asp Pro Ser Gln Val Ser His Gly Thr Gly
                    195                 200                 205

Phe Thr Ser Phe Gly Leu Leu Lys Leu
                210                 215

<210> SEQ ID NO 9
<211> LENGTH: 154
<212> TYPE: PRT
<213> ORGANISM: Homo sapiens

<400> SEQUENCE: 9

Glu Asn Ser Phe Glu Met Gln Lys Gly Asp Gln Asn Pro Gln Ile Ala
     1               5                   10                  15
```

```
Ala His Val Ile Ser Glu Ala Ser Ser Lys Thr Thr Ser Val Leu Gln
            20                  25                  30

Trp Ala Glu Lys Gly Tyr Tyr Thr Met Ser Asn Asn Leu Val Thr Leu
        35                  40                  45

Glu Asn Gly Lys Gln Leu Thr Val Lys Arg Gln Gly Leu Tyr Tyr Ile
50                  55                  60

Tyr Ala Gln Val Thr Phe Cys Ser Asn Arg Glu Ala Ser Ser Gln Ala
65                  70                  75                  80

Pro Phe Ile Ala Ser Leu Cys Leu Lys Ser Pro Gly Arg Phe Glu Arg
                85                  90                  95

Ile Leu Leu Arg Ala Ala Asn Thr His Ser Ser Ala Lys Pro Cys Gly
            100                 105                 110

Gln Gln Ser Ile His Leu Gly Gly Val Phe Glu Leu Gln Pro Gly Ala
        115                 120                 125

Ser Val Phe Val Asn Val Thr Asp Pro Ser Gln Val Ser His Gly Thr
130                 135                 140

Gly Phe Thr Ser Phe Gly Leu Leu Lys Leu
145                 150

<210> SEQ ID NO 10
<211> LENGTH: 149
<212> TYPE: PRT
<213> ORGANISM: Homo sapiens

<400> SEQUENCE: 10

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
130                 135                 140

Gly Leu Leu Lys Leu
145

<210> SEQ ID NO 11
<211> LENGTH: 15
<212> TYPE: PRT
<213> ORGANISM: Homo sapiens

<400> SEQUENCE: 11

Glu Pro Lys Ser Cys Asp Lys Thr His Thr Cys Pro Pro Cys Pro
1               5                   10                  15

<210> SEQ ID NO 12
```

```
<211> LENGTH: 5
<212> TYPE: PRT
<213> ORGANISM: Artificial Sequence
<220> FEATURE:
<223> OTHER INFORMATION: linker

<400> SEQUENCE: 12

Gly Gly Gly Gly Ser
1               5

<210> SEQ ID NO 13
<211> LENGTH: 5
<212> TYPE: PRT
<213> ORGANISM: Artificial Sequence
<220> FEATURE:
<223> OTHER INFORMATION: linker

<400> SEQUENCE: 13

Gly Gly Gly Gly Ser
1               5

<210> SEQ ID NO 14
<211> LENGTH: 37
<212> TYPE: PRT
<213> ORGANISM: Artificial Sequence
<220> FEATURE:
<223> OTHER INFORMATION: linker

<400> SEQUENCE: 14

Gly Asp Pro Leu Val Thr Ala Ala Ser Val Leu Glu Phe Gly Gly Ser
1               5                  10                  15

Gly Gly Gly Ser Glu Gly Gly Ser Glu Gly Gly Ser Glu Gly
            20                  25                  30

Gly Gly Ser Asp Ile
        35

<210> SEQ ID NO 15
<211> LENGTH: 247
<212> TYPE: PRT
<213> ORGANISM: Artificial Sequence
<220> FEATURE:
<223> OTHER INFORMATION: linker

<400> SEQUENCE: 15

Glu Pro Lys Ser Cys Asp Lys Thr His Thr Cys Pro Pro Cys Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Glu Pro Lys Ser Cys Asp Lys Thr
225                 230                 235                 240

His Thr Cys Pro Pro Cys Pro
                245

<210> SEQ ID NO 16
<211> LENGTH: 230
<212> TYPE: PRT
<213> ORGANISM: Artificial Sequence
<220> FEATURE:
<223> OTHER INFORMATION: linker

<400> SEQUENCE: 16

Glu Pro Lys Ser Ser Asp Lys Thr His Thr Ser Pro Pro Ser Pro Ala
1               5                   10                  15

Pro Pro Val Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro
225                 230

<210> SEQ ID NO 17
```

<211> LENGTH: 183
<212> TYPE: PRT
<213> ORGANISM: Homo sapiens

<400> SEQUENCE: 17

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 18
<211> LENGTH: 261
<212> TYPE: PRT
<213> ORGANISM: Homo sapiens

<400> SEQUENCE: 18

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

-continued

```
Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
            245                 250                 255

Gly Leu Leu Lys Leu
            260
```

AGONIST FUSION PROTEIN FOR CD40 AND OX40 AND METHODS OF STIMULATING THE IMMUNE SYSTEM

CROSS REFERENCE TO RELATED APPLICATION

This application is a 35 U.S.C. § 371 national phase application from, and claims priority to, International Application No. PCT/US2014/014200, filed Jan. 31, 2014, and published under PCT Article 21(2) in English, which claims the benefit of U.S. Provisional Application No. 61/759,326, filed Jan. 31, 2013, the entire disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 30, 2014, is named 37075_0293_00_WO_SeqListing_ST25, and is 22,470 bytes in size.

FIELD OF THE INVENTION

The present invention relates to fusion proteins comprising an agonist for CD40 and an agonist for OX40.

BACKGROUND OF THE INVENTION

Members of the TNF (Tumor necrosis factor) ligand/TNF receptor superfamily play key roles in a large number of biological events. For instance, members of the TNF ligand/TNF receptor superfamily figure prominently in the complex interplay of positive and negative signals that regulate T cell activation, maintenance of T cell effector function, promotion of maturation of antigen-presenting cells (APCs), such as dendritic cells, and the T cell stimulation of APCs.

TNF receptors are broadly classified in three groups (Dempsey et al., 2003, "The signaling adaptors and pathways activated by TNF superfamily," Cytokine Growth Factor Rev. 14(3-4):193-209). Receptors in the first group contain a death domain in their cytoplasmic tails. Receptors in the second group contain a TRAF interaction motif in their cytoplasmic tails. The third group of TNF receptors do not contain functional intracellular signaling domains but can act as decoy receptors.

There are nearly two dozen TNF receptors in the second group. From the standpoint of immune activation, OX40 and CD40 are of interest.

OX40 is a cell surface glycoprotein that is expressed primarily on activated CD4+ T cells and some human T cell leukemia virus type I (HTLV-I)-infected T cell lines, but is not typically expressed on resting naïve T cells, resting peripheral T cells, peripheral B cells, or thymocytes. OX40 is a costimulatory molecule that is expressed about 24 to 72 hours after activation of T cells. OX40 ligand ("OX40L") is expressed on activated APCs but not on resting APCs. Binding of OX40L to OX40 on activated T cells prevents activated T cells from dying and subsequently increases cytokine production. As a result of enhancing survival of activated T cells, OX40 thus plays an important role in maintaining an immune response beyond the first few days and leads to a memory response.

CD40 is also a cell surface glycoprotein. CD40 is expressed on a variety of cells in the immune system, such as B cells, dendritic cells, macrophages, and monocytes. CD40 is not only expressed by normal immune cells, but also by many malignant cells.

CD40 ligand ("CD40L") is the cognate ligand for CD40 and is expressed primarily by activated T cells. Binding of CD40L to CD40 on non-tumor cells results in proliferation of the cells. In contrast, binding of CD40L to CD40 on tumor cells often results in tumor cell apoptosis. Reviews of the CD40/CD40 ligand signaling axis are available. See, e.g., van Kooten et al., 2000, *J Leukoc Biol.* 67(1): 2-17.

The biological activities of the CD40/CD40L axis and, separately, the OX40/OX40L axis, have led to the suggestion of various therapeutic agents. There is a need in the art for improved therapeutics pertaining to these signaling axes.

SUMMARY OF THE INVENTION

Provided is a fusion protein comprising Component A and Component B, wherein Component A comprises a polypeptide agonist for OX40 and Component B comprises a polypeptide agonist for CD40, and optionally comprising a linker between Components A and B. In some embodiments, the N-terminus of Component A is fused to the C-terminus of Component B, either directly or indirectly, via the linker. In other embodiments, the N-terminus of Component B is fused to the C-terminus of Component A, either directly or indirectly, via the linker.

In any of the above embodiments, the polypeptide agonist for OX40 may comprise, or example, at least a portion of the ectodomain of OX40 ligand (OX40L). In some embodiments, the ectodomain is from human OX40L. In any of the above embodiments, the polypeptide agonist for OX40 may comprise, for example, a sequence selected from SEQ ID NO: 2, SEQ ID NO: 3, and SEQ ID NO. 17. Alternatively, the polypeptide agonist for OX40 is a derivative of an agonist monoclonal anti-OX40 antibody, the derivative selected from scFvOX40, $V_H C_H OX40$, and $V_H HOX40$, or example.

In any of the above embodiments, the polypeptide agonist for CD40 may comprise, for example, at least a portion of the ectodomain of CD40 ligand (CD40L). In some embodiments, the ectodomain is from human CD40L. In any of the above embodiments, the polypeptide agonist for CD40 may comprise, for example, a sequence selected from SEQ ID NO: 8, SEQ ID NO: 9, SEQ ID NO: 10, and SEQ ID NO. 18. Alternatively, the polypeptide agonist for CD40 is a derivative of an agonist monoclonal anti-CD40 antibody, the derivative selected from scFvCD40, $V_H C_H CD40$, and $V_H HCD40$, for example.

In some embodiments, the polypeptide agonist for CD40 is a derivative of an agonist monoclonal anti-CD40 antibody, the derivative selected from scFvCD40, $V_H C_H CD40$, and $V_H HCD40$, and the polypeptide agonist for OX40 comprises at least a portion of the ectodomain of OX40L; and the N-terminus of Component B is fused to the C-terminus of Component A, either directly or indirectly via the linker.

In further embodiments, the fusion protein comprises at least a portion of SEQ ID NO: 2, SEQ ID NO: 3, SEQ ID NO: 8, SEQ ID NO: 9, SEQ ID NO: 10, SEQ ID NO: 17, or SEQ ID NO: 18.

In any of the above described embodiments, the linker may comprise, for example, one of:

```
                                    (SEQ ID NO: 14)
GDPLVTAASVLEFGGSGGGSEGGGSEGGGSEGGGSDI, (SEQ ID NO: 15)
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK
```

-continued

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGKEPKSCDKTHTCPPCP
and (SEQ ID NO: 16)
EPKSSDKTHTSPPSPAPPVAGAPSVFLFPPKPKDTLMISRTPEVTCVVVDV

SHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK.

In further embodiments, the fusion protein consists of Component A and Component B, wherein Component A comprises a polypeptide agonist for OX40 and Component B comprises a polypeptide agonist for CD40, and optionally comprises a linker between Components A and B.

Also provided is a pharmaceutical composition comprising a pharmaceutically acceptable carrier and the fusion protein of any of the embodiments disclosed herein.

Further provided is a method of stimulating the immune system of a patient. The method comprises administering an therapeutically effective amount of the fusion protein of any of the embodiments disclosed herein to a patient in need of such treatment. In some embodiments of the method, the administering step further comprises administering a vaccine to the patient. In some embodiments, the fusion protein and the vaccine are administered simultaneously. In other embodiments, the fusion protein and the vaccine are administered sequentially.

Also provided is a method of treating a proliferative disorder in a patient. The method comprises administering a therapeutically effective amount of the fusion protein of any of the embodiments disclosed herein to a patient in need of such treatment. In some embodiments, the proliferative disorder is cancer. In further embodiments, the cancer is one of a hematological B cell malignancy and melanoma.

Further provided is a method of treating a persistent viral infection in a patient, the method comprising administering a therapeutically effective amount of the fusion protein of any of the embodiments disclosed herein to a patient in need of such treatment. In some embodiments, the persistent viral infection is one of chronic hepatitis, herpes virus-induced disease, and HIV/AIDS.

Further provided is a fusion protein of any one of the preceding embodiments disclosed herein, for use (i) in medicine, (ii) treating a proliferative disorder, (iii) treating a persistent viral infection, or (iv) stimulating the immune system. Provided is a genetic sequence encoding a fusion protein of any one of the preceding fusion protein embodiments, for use in medicine; for use in treating a proliferative disorder, such as cancer; for use in treating a persistent viral infection; or for use in stimulating the immune system.

BRIEF DESCRIPTION OF THE DRAWINGS

FIG. 2 depicts schematic drawings of various embodiments of the fusion protein of the invention in the Component B-Component A configuration.

DEFINITIONS

Figures 1A, 1B, 1C, 1D, 1E:
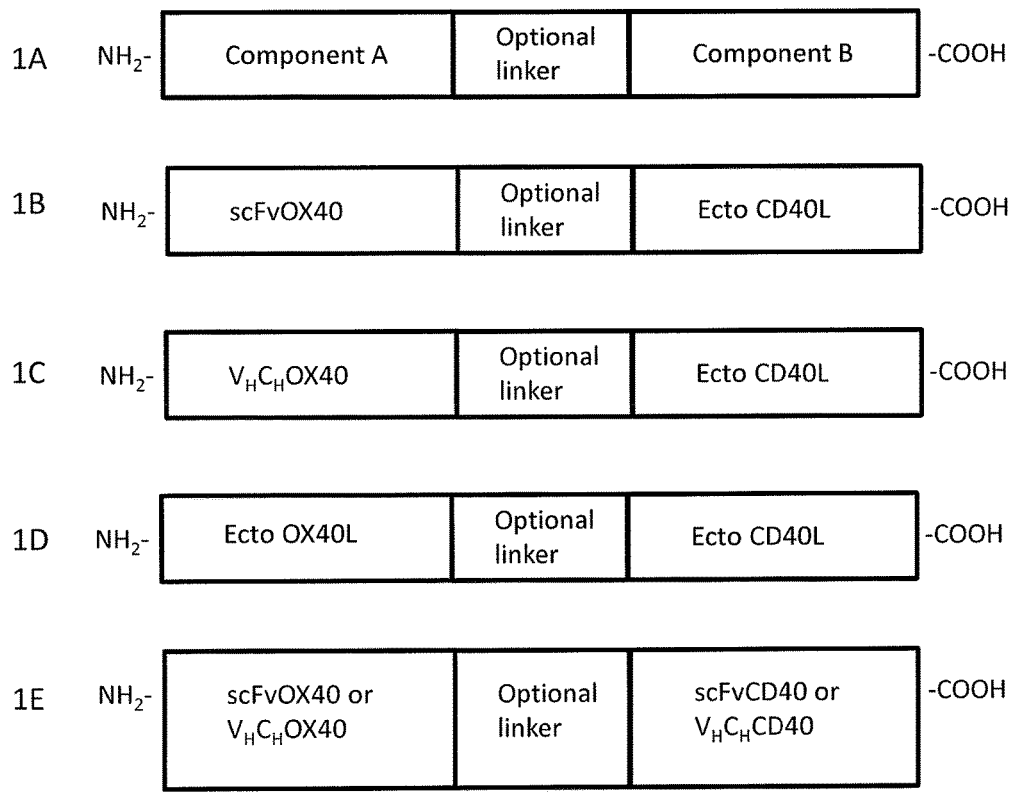
FIG. 1 depicts schematic drawings of various embodiments of the fusion protein of the invention in the Component A-Component B configuration.

As used in the specification and the appended claims, the singular forms "a," "an" and "the" include plural referents unless the context clearly dictates otherwise.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

A "fusion protein" or "fusion polypeptide" is a polypeptide comprised of at least two polypeptides and optionally a linking sequence, and that are operatively linked into one continuous protein. The two polypeptides linked in a fusion protein are typically derived from two independent sources, and therefore a fusion protein comprises two linked polypeptides not normally found linked in nature. Typically, the two polypeptides can be operably attached directly by a peptide bond.

The term "operably linked," as used herein, indicates that two molecules (e.g., polypeptides) are attached so as to each retain biological activity. Two molecules are "operably linked" whether they are attached directly or indirectly (e.g., via a linker).

The term "linker" as used herein refers to a peptide that is optionally located between two amino acid sequences in the fusion protein of the invention.

As used herein, a "biologically active" or "immunologically active" as applied to a fusion protein refers to a fusion protein according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild-type proteins which are the building blocks of the fusion protein.

As used herein, "OX40" refers to a cell surface glycoprotein that is a member of the tumor necrosis factor receptor family. Other names in the art for OX40 include: CD134, TNFRSF4, ACT35, ACT-4, and TXGP1L. An exemplary protein sequence for human OX40 is GENBANK® Accession no. NP_003318.1 (sequence includes signal peptide), which is encoded by nucleic acid sequence GENBANK® Accession no. NM_003327.3.

As used herein, "trigger" with respect to a receptor, such as OX40 or CD40, refers to the biological change that occurs upon ligation of the receptor by an agonist ligand. Biological changes that can occur when a receptor is triggered include, but are not limited to, one or more of: receptor interaction with one or more intracellular adaptors and effector molecules; induction of a signaling cascade; modified expression of molecules; release of cytokines and/or chemokines; activation of caspases; activation of transcription factors; changes in protein modification such as a phosphorylation; activation of signal transduction pathways such as NF-κB and P13K; induction of downstream effects on transcriptional, translational, and post-translational control mechanisms affecting one or more genes and/or proteins expressed by the cell.

As used herein, "OX40 ligand" refers to a cell surface glycoprotein that is a member of the tumor necrosis factor ligand family. OX40 ligand is the cognate ligand for OX40. Other names in the art for OX40 ligand include: OX40L, CD252, TNFSF4, TXGP1, and gp32. An exemplary protein sequence for human OX40L is GENBANK® Accession no.

NP_003317.1, which is encoded by nucleic acid sequence GENBANK® Accession no. NM_003326.3.

As used herein, "CD40" refers to a cell surface glycoprotein that is a member of the tumor necrosis factor receptor family. Other names in the art for CD40 include: TNFRSF5, p50, CDW40 and Bp50. An exemplary protein sequence for human CD40 is GENBANK® Accession no. AAH12419.1 (sequence includes signal peptide), which is encoded by nucleic acid sequence GENBANK® Accession no. BC012419.1.

As used herein, "CD40 ligand" refers to a cell surface glycoprotein that is a member of the tumor necrosis factor ligand family. CD40 ligand is the cognate ligand for CD40. Other names in the art for CD40 ligand include: CD40L, CD40LG, CD154, TNFSF5, TRAP, gp39, HIGM1, IGM, IMD3, and T-BAM. An exemplary protein sequence for human CD40L is NP_000065.1, which is encoded by nucleic acid sequence NM_000074.2.

As used herein, the term "agonist" refers to a compound that in combination with a receptor can produce a cellular response. An agonist may be a ligand that directly binds to the receptor. Alternatively an agonist may combine with a receptor indirectly by for example (a) forming a complex with another molecule that directly binds to the receptor, or (b) otherwise resulting in the modification of another compound so that the other compound directly binds to the receptor.

The term "CD40 agonist" in particular includes any entity which agonizes CD40. This includes CD40 agonistic antibodies and fragments thereof, and soluble CD40L and fragments and derivatives thereof.

The term "OX40 agonist" in particular includes any entity which agonizes OX40. This includes OX40 agonistic antibodies and fragments thereof; and soluble OX40L and fragments and derivatives thereof.

The term "antibody," as used herein, refers to an immunoglobulin molecule which is able to specifically bind to a specific epitope on an antigen, as well as fragments and derivatives of thereof, which fragments and derivatives have at least an antigenic binding site. Antibodies can be intact immunoglobulins derived from natural sources or from recombinant sources and can be immunoreactive portions of intact immunoglobulins. Antibodies are typically tetramers of immunoglobulin molecules. Antibodies may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies such as camelid antibodies, chimeric antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879-5883; Bird et al., 1988, *Science* 242:423-426).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

The term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

As used herein, the term "agonist CD40 antibody" or "agonist anti-CD40 antibody" means an antibody that specifically binds to an CD40 molecule, such as human CD40, and increases one or more CD40 activities by at least about 20% when added to a cell, tissue or organism expressing CD40. In some embodiments, the antibody activates CD40 activity by at least 40%, 50%, 60%, 70%, 80%, or 85%.

As used herein, the term "agonist OX40 antibody" or "agonist anti-OX40 antibody" means an antibody that specifically binds to a OX40 molecule, such as human OX40, and increases one or more OX40 activities by at least about 20% when added to a cell, tissue or organism expressing OX40. In some embodiments, the antibody activates OX40 activity by at least 40%, 50%, 60%, 70%, 80%, or 85%.

A polypeptide having an "ectodomain" is one wherein a portion of the polypeptide is positioned within a cellular membrane and a portion of the polypeptide is located on the outside of a cell. Typically, the polypeptide spans the cell membrane of a cell. Thus, by the term "ectodomain" of a polypeptide is meant that portion of a polypeptide which is located on the outside of a cell (i.e., extracellular domain), where another portion of the polypeptide spans or is otherwise located within the cell membrane.

As used herein, a "deletion" in an amino acid sequence or polypeptide is defined as a change in amino acid sequence in which one or more amino acid residues are absent as compared to the wild-type protein.

As used herein an "insertion" or "addition" in an amino acid sequence or polypeptide is a change in an amino acid sequence that has resulted in the addition of one or more amino acid residues as compared to the wild-type protein.

As used herein "substitution" in an amino acid sequence or polypeptide results from the replacement of one or more amino acids by different amino acids, respectively, as compared to the wild-type protein.

As used herein, the term "variant" with respect to an amino acid sequence or polypeptide means any polypeptide having a substitution of, deletion of or addition of one (or more) amino acid from or to the sequence, including allelic variations, as compared with the wild-type protein, so long as the resultant variant fusion protein retains at least 75%, 80%, 85%, 90%, 95%, 96%, 97%, 98%, 99% or more of the biological or immunologic activity as compared to the wild-type proteins as used in the present invention. Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity. Furthermore, variants or derivatives can be generated that would have altered multimerization properties. When engineering variants, for instance, of CD40 ligand, this could be done for either the entire CD40L soluble ectodomain, or for that component of the ectodomain that is incorporated within the fusion protein itself.

Sequence identity or homology can be determined using standard techniques known in the art, such as the Best Fit sequence program described by Devereux et al., *Nucl. Acid Res.* 12:387-395 (1984) or the BLASTX program (Altschul et al., *J. Mol. Biol.* 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids.

Preferably, variants or derivatives of the fusion proteins of the present invention maintain the hydrophobicity/hydrophilicity of the parent amino acid sequence. Conservative amino acid substitutions may be made, for example from 1, 2 or 3 to 10, or 30 substitutions provided that the modified sequence retains the ability to act as a fusion protein in accordance with present invention. Amino acid substitutions may include the use of non-naturally occurring analogues, for example to increase blood plasma half-life.

Conservative substitutions are known in the art, for example according to the table below. Amino acids in the same block in the second column and preferably in the same line in the third column may be substituted for each other:

| ALIPHATIC | Non-polar | GAPILV |
|---|---|---|
|  | Polar- | CSTM |
|  | Uncharged | NQ |
|  | Polar-charged | DE |
|  |  | KR |
| AROMATIC |  | HFWY |

The term "derivative" as used herein in relation to an amino acid sequence means chemical modification of a fusion protein of the invention.

The term "derivative" in the context of an antibody refers to a portion of an immunoglobulin having at least an antigenic binding site. Examples include, but are not limited to, intracellular antibodies ("intrabodies"), Fv, Fab and F(ab)$_2$, as well as single chain antibodies (scFv), heavy chain antibodies such as camelid antibodies, chimeric antibodies, and humanized antibodies.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein."

As used herein, a polypeptide is "soluble" when it lacks any transmembrane domain or peptide domain that anchors or integrates the polypeptide into the membrane of a cell expressing such polypeptide. In particular, the soluble proteins useful as components in the fusion protein of the invention may exclude transmembrane and intracellular domains. The soluble proteins may comprise substantially all of an ectodomain or may comprise a fragment thereof possessing the required agonist function, e.g., a functional fragment.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "vaccine" as used herein is defined as a material used to provoke an immune response after administration of the material to a mammal. The material used to provoke the immune response can comprise, for instance, a pathogen or an antigenic portion thereof or a cancer antigen.

The term "virus" as used herein is defined as a particle consisting of nucleic acid (RNA or DNA) enclosed in a protein coat, with or without an outer lipid envelope, which is capable of replicating within a whole cell.

As used herein, a "therapeutically effective amount" is the amount of a composition sufficient to provide a beneficial effect to a mammal to which the composition is administered. A therapeutically effective amount of a fusion protein of the invention is an amount that will ameliorate one or more of the well-known parameters that characterize medical conditions caused by, an insufficient immune response, for instance, a tumor or a persistent viral infection. Many such parameters and conditions have been described and are well known to the skilled artisan. A therapeutically effective amount, in the context of a tumor or a persistent viral infection, will be the amount of fusion protein that is sufficient to accomplish one or more of the following: decrease the severity of symptoms; decrease tumor size; decrease rate of tumor growth; decrease the duration of disease exacerbations; increase the frequency and duration of disease remission/symptom-free periods; and/or prevent/attenuate chronic progression of the disease. A therapeutically effective amount of a fusion protein of the invention also encompasses an amount that will increase the immune response of a subject to a vaccine, e.g., a malaria vaccine or a cancer vaccine, when the fusion protein is administered as an adjuvant for the vaccine. Many such parameters and conditions have been described and are well known to the skilled artisan. A therapeutically effective amount of the fusion protein as a vaccine adjuvant, will be the amount of fusion protein that is sufficient to accomplish one or more of the following: improve immune response to vaccine antigen and/or to subsequent presentation of antigen; broaden the immune response of the subject to a wider range of antigens in the vaccine; speed up the development of immune response to vaccine antigens; and increase the specificity of the subject's immune response to vaccine antigens.

"Treating" or "treatment," refers to a therapeutic treatment, wherein the object is to prevent or slow down (lessen) the targeted pathologic condition or disorder. A subject is "treated" if: after receiving a therapeutic amount of a fusion protein of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Treatment can achieve a complete response, defined as disappearance of all signs of cancer, or a partial response, wherein the size of the tumor is decreased, preferably by more than 50%, more preferably by 75%. A patient is also considered treated if the patient experiences a stabilization of disease.

As used herein, "stimulating the immune system" refers to a therapeutic treatment, wherein the object is to improve one or more aspects of immune function. A subject has their immune system stimulated if: after receiving a therapeutic amount of a fusion protein of the invention according to the methods of the present invention, the subject shows observable and/or measurable increase in one or more parameters of the immune system. Such parameters include, for example: an increase in the number and/or activity of immune cells responsive to a specific pathogen, or antigenic part thereof; an increase in the rate of development of immune cells responsive to a specific pathogen, or antigenic part thereof, or cancer antigen; or a reduction in an immune response time after subsequent exposure to a specific pathogen, or antigenic part thereof, or cancer antigen. In the context of a cancer antigen, a subject is considered to have their immune system stimulated if there is observable and/or measurable reduction in or absence of one or more signs and symptoms of the particular cancer associated with the cancer antigen, as discussed above.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein with respect to polynucleotides means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The phrase "persistent viral infection" as used herein, refers to a viral infection where the infectious agent and/or infected cells are not entirely cleared from the body. Persistent viral infections occur when the primary infection is not cleared, for instance, by the adaptive immune response. Examples of viruses that cause persistent infections include, but are not limited to: herpes simplex virus-1, herpes simplex virus-2, varicella-zoster virus, measles virus, HIV-1, hepatitis B, C, D and E, and human cytomegalovirus. A chronic viral infection is a type of persistent infection that is eventually cleared. Persistent viral infections also include latent or slow infections that last the life of the host.

As used herein in the specification and claims, including as used in the examples and unless otherwise expressly specified, all numbers may be read as if prefaced by the word "about," even if the term does not expressly appear.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK® Accession number, the sequence is incorporated herein in its entirety by reference. Information associated with the accession number, such as identification of signal peptide, extracellular domain, transmembrane domain, promoter sequence and translation start, is also incorporated herein in its entirety by reference.

As envisioned in the present invention with respect to the disclosed compositions of matter and methods, in one aspect, the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DETAILED DESCRIPTION OF THE INVENTION

The present invention provides a fusion protein that acts on the OX40 signaling axis and the CD40 signaling axis. The fusion protein comprises a Component A and a Component B, wherein Component A comprises a polypeptide agonist for OX40 and Component B comprises a polypeptide agonist for CD40. Binding of Component A to OX40 triggers OX40 signaling in an OX40-expressing cell. Binding of Component B to CD40 triggers CD40 signaling in a CD40-expressing cells.

Component A: OX40 Agonist

Suitable polypeptide agonists for OX40 include, for example, the OX40 ligand (OX40L) itself, variants or derivatives of the wild-type OX40L, and agonist antibodies to OX40 and antibody derivatives comprising functional fragments thereof. In one embodiment, Component A comprises the ectodomain of OX40L, or a functional fragment thereof. In another embodiment, Component A comprises an antibody derivative of an agonist monoclonal anti-OX40 antibody that induces OX40 signaling upon binding to OX40. Variants of the wild-type form of the OX40L ectodomain are also included in the present invention, or the portion of the ectodomain responsible for OX40L binding, so long as the variant provides a similar level of biological activity as the wild-type protein for triggering OX40.

In one embodiment, the agonist for OX40 is derived from a monoclonal antibody that specifically binds to OX40 and triggers OX40 signaling. In an embodiment, the agonist for OX40 is a single chain variable fragment (scFv) comprising a $V_H$ domain and a $V_L$ domain from an agonist monoclonal anti-OX40 antibody. This agonist antibody derivative is referred to herein as "scFvOX40." In another embodiment, the agonist for OX40 comprises a $V_H$ domain and heavy chain constant region from an agonist monoclonal anti-OX40 antibody. This agonist antibody derivative is referred to herein as "$V_H C_H OX40$." For embodiments wherein the agonist for OX40 comprises $V_H C_H OX40$, a polypeptide comprising a $V_L$ domain and light chain constant region from the agonist monoclonal anti-OX40 antibody, referred to herein as "$V_L C_L OX40$," is optionally provided in trans.

Agonist monoclonal anti-OX40 antibodies are known in the art. For instance, Bakker et al. (U.S. Pat. No. 7,55,140) teach scFv's against OX40 that bind to and trigger OX40, and a method for obtaining such scFv's. Croft et al. (U.S. Pat. No. 8,283,450) teach monoclonal antibodies against human OX40, including agonist antibodies and fragments thereof, and methods for obtaining agonist anti-OX40 antibodies. Croft et al. further teach exemplary epitopes in the ectodomain of OX40 useful for preparing monoclonal antibodies.

In another embodiment, the agonist for OX40 is a $V_H H$ (camelid heavy chain antibody). This agonist antibody form is referred to herein as "$V_H HOX40$."

Agonist monoclonal antibodies against non-human OX40 may also be used in the practice of the invention, provided they bind and trigger OX40 in the recipient of the fusion protein.

The skilled artisan can make monoclonal antibodies to OX40 using conventional methods described elsewhere herein. A suitable antigen for preparing monoclonal antibodies is the ectodomain of OX40. An exemplary sequence for the ectodomain of human OX40 is: VTGLHCVGD- TYPSNDRCCHECRPGNGMVSRCSRSQNTVCRPCGP-
GFYNDVVSSKPCK PCTWCNLRSGSERKQLCTATQ D-
TVCRCRAGTQPLDSYKPGVDCAPCPPGHFSPGDNQ
ACKPWTNCTLAGKHTLQPASNSSDAICEDRDPPAT-
QPQETQGPPARPITVQPTEAWPR TSQGPS (SEQ ID
NO: 1). Methods of assessing whether a monoclonal antibody against OX40 is an agonist are known in the art. Exemplary methods include, but are not limited to, assaying a candidate monoclonal OX40 antibody's ability to enhance activity, such as proliferation, signaling, effector function, and cytokine production, of activated $CD4^+$ T-cells. See, for instance, Bakker et al. (U.S. Pat. No. 7,55,140).

In another embodiment, the agonist for OX40 is a functional fragment of OX40L. Preferably, the functional fragment of OX40L is a soluble form ("sOX40L"), such as the ectodomain of OX40L, or a biologically active fragment thereof. As used herein, the term "biological active fragment thereof" in the context of the ectodomain of OX40L encompasses any fragment of the ectodomain that can specifically bind to OX40 and trigger OX40 signaling. An exemplary sequence for the ectodomain of human OX40L is:

(SEQ ID NO: 2)
FSALQVSHRYPRIQSIKVQFTEYKKEKGFILTSQKEDEIMKVQNNSVIINC

DGFYLISLKGYFSQEVNISLHYQKDEEPLFQLKKVRSVNSLMVASLTYKDK

VYLNVTTDNTSLDDFHVNGGELILIHQNPGEFCVL.

Another exemplary sequence for the ectodomain of human OX40L is:

(SEQ ID NO: 3)
PRIQSIKVQFTEYKKEKGFILTSQKEDEIMKVQNNSVIINCDGFYLISLKG

YFSQEVNISLHYQKDEEPLFQLKKVRSVNSLMVASLTYKDKVYLNVTIDNT

SLDDFHVNGGELILIHQNPGEFCVL.

In some embodiments, the agonist for OX40 comprises the ectodomain of the human OX40L. In other embodiments, the agonist for OX40 comprises a fragment of the OX40L comprising at least 20, 30, 40, 50, 60, 70, 80, 90, 100, 110, 120, 130, 140, 150, 160, 170, 180, or 182 contiguous amino acids of the full-length OX40L protein, wherein the fragment binds to and triggers OX40.

Component B: CD40 Agonist

Suitable polypeptide agonists for CD40 include, for example, the CD40 ligand (CD40L) itself, variants or derivatives of the wild-type CD40L, and agonist antibodies to CD40 and antibody derivatives comprising functional fragments thereof. In one embodiment, Component B comprises the ectodomain of CD40L, or a functional fragment thereof. In another embodiment, Component B comprises a derivative of an agonist monoclonal anti-CD40 antibody that triggers CD40 signaling upon binding to CD40. Variants of the wild-type form of the CD40L ectodomain are also included in the present invention, or the portion of the ectodomain responsible for CD40L binding, so long as the variant provides a similar level of biological activity as the wild-type protein for triggering CD40.

In one embodiment, the agonist for CD40 is derived from a monoclonal antibody that specifically binds to CD40 and triggers CD40 signaling. In an embodiment, the agonist for CD40 is a single chain variable fragment (scFv) comprising a $V_H$ domain and a $V_L$ domain from an agonist monoclonal anti-CD40 antibody. This agonist antibody derivative is referred to herein as "scFvCD40." In another embodiment, the agonist for CD40 comprises a $V_H$ domain and heavy chain constant region from an agonist monoclonal anti-CD40 antibody. This agonist antibody derivative is referred to herein as "$V_H C_H$CD40." For embodiments wherein the agonist for CD40 comprises $V_H C_H$CD40, a polypeptide comprising a$V_L$ domain and light chain constant region from an agonist monoclonal anti-CD40 antibody, referred to herein as "$V_L C_L$CD40" is optionally provided in trans.

Agonist monoclonal anti-CD40 antibodies are known in the art. For instance, Zhang et al. (WO2012149356A2) teach a monoclonal antibody against CD40 and fragments thereof that are capable of binding to CD40 and function as CD40 agonists by inducing/enhancing CD40-mediated downstream cell signaling and biological effects. Similarly, Gladue et al. (US20120263732A1) also disclose monoclonal antibodies against CD40, and fragments thereof that are capable of binding to CD40 and function as CD40 agonists by inducing/enhancing CD40-mediated downstream cell signaling and biological effects. Pfizer Inc. has developed a fully human $IgG_2$ CD40 agonist antibody, CP-870,893 (Gladue et al., 2011, "The CD40 agonist antibody CP-870,893 enhances dendritic cell and B-cell activity and promotes anti-tumor efficacy in SCID-hu mice," Cancer Immunol Immunother. 60(7):1009-17. doi:10.1007/s00262-011-1014-6. Epub 2011 Apr. 12. PubMed PMID: 21479995).

An exemplary monoclonal anti-human CD40 antibody is G28-5. G28-5 is a mouse monoclonal anti-human CD40 antibody (commercially available, for instance, from BioLegend®, San Diego, Calif.) that is an agonist of human CD40 (Clark et al., 1986, "Activation of human B cells mediated through two distinct cell surface differentiation antigens, Bp35 and Bp50," Proc Natl Acad Sci USA. 83(12): 4494-4498). The amino acid sequence of the light chain variable region precursor of G28-5 is provided in GENBANK® Accession No. AAB81500.1. The mature peptide contains residues 20-131 and has the sequence:

(SEQ ID NO:. 4)
DAVMTQNPLSLPVSLGDEASISCRSSQSLENSNGNTFLNWFFQKPGQSPQL

LIYRVSNRFSGVPDRFSGSGSGTDFTLKISRVEAEDLGVYFCLQVTHVPYT

FGGGTTLEIK.

The amino acid sequence of the heavy chain variable region precursor of G28-5 is provided in GENBANK® Accession No. AAB81501.1. The mature peptide contains residues 19-130 of the sequence and has the sequence:

(SEQ ID NO: 5)
DIQLQQSGPGLVKPSQSLSLTCSVTGYSITTNYNWNWIRQFPGNKLEWMGY

IRYDGTSEYTPSLKNRVSITRDTSMNQFFLRLTSVTPEDTATYYCARLDYW

GQGTSVTVSS.

G28-5 has been used to prepare an antibody derivation, e.g., scFvCD40, in the art (see, e.g., Francisco et al., 1995, "Activity of a single-chain immunotoxin that selectively kills lymphoma and other B-lineage cells expressing the CD40 antigen," Cancer Res. 55(14):3099-104).

Agonist monoclonal antibodies against non-human CD40 may also be used in the invention, provided they bind and trigger CD40 in the recipient of the fusion protein.

In another embodiment, the agonist for CD40 is a $V_H$H (camelid heavy chain antibody). This agonist antibody derivative is referred to herein as "$V_H$HCD40."

The skilled artisan can make monoclonal antibodies to CD40 using conventional methods described elsewhere herein and in the prior art. See, for instance, Zhang et al. (WO2012149356A2) and Gladue et al. (US20120263732A1). A suitable antigen for preparing monoclonal antibodies is the ectodomain of CD40. An exemplary sequence for the ectodomain of human CD40 is:

(SEQ ID NO: 6)
EPPTACREKQYLINSQCCSLCQPGQKLVSDCTEFTETECLPCGESEFLDTW

NRETHCHQHKYCDPNLGLRVQQKGTSETDTICTCEEGWHCTSEACESCVLH

RSCSPGFGVKQIATGVSDTICEPCPVGFFSNVSSAFEKCHPWTSCETKDLV

VQQAGTNKTDVVCGPQDR.

Another exemplary sequence for the ectodomain of human CD40 is:

(SEQ ID NO: 7)
CREKQYLINSQCCSLCQPGQKLVSDCTEFTETECLPCGESEFLDTWNRETH

CHQHKYCDPNLGLRVQQKGTSETDTICTCEEGWHCTSEACESCVLHR.

Methods of assessing whether a monoclonal antibody against CD40 is an agonist are known in the art. Exemplary methods include, but are not limited to, screening candidate monoclonal CD40 antibodies for dendritic cell maturation and/or for the ability to induce the tumor growth inhibition of CD40-expressing tumor cells as taught by Zhang et al. (WO2012149356A2); and measuring activity in a whole blood surface molecule upregulation assay; performing to a dendritic cell assay to measure IL-12 release; and/or measuring activity in an in vivo tumor model as taught by Gladue et al. (US20120263732A1). In another embodiment, the activity of the activating antibody can be measured using a dendritic cell assay to measure IL-12 release. In another embodiment, the activity of the activating antibody can be measured using an in vivo tumor model.

In another embodiment, the agonist for CD40 is a functional fragment of CD40L. Preferably, the functional fragment of CD40L is a soluble form ("sCD40L"), such as the ectodomain of CD40L, or a biologically active fragment thereof. As used herein, the term "biological active fragment thereof" in the context of the extracellular domain of CD40L encompasses any fragment of the ectodomain that can specifically bind to CD40 and trigger CD40 signaling. An exemplary sequence for the ectodomain of human CD40L is:

(SEQ ID NO: 8)
YLHRRLDKIEDERNLHEDFVFMKTIQRCNTGERSLSLLNCEEIKSQFEGFV

KDIMLNKEETKKENSFEMQKGDQNPQIAAHVISEASSKTTSVLQWAEKGYY

TMSNNLVTLENGKQLTVKRQGLYYIYAQVTFCSNREASSQAPFIASLCLKS

PGRFERILLRAANTHSSAKPCGQQSIHLGGVFELQPGASVFVNVTDPSQVS

HGTGFTSFGLLKL.

Fragments of the CD40L ectodomain are known to bind CD40 and trigger CD40 signaling. An exemplary CD40L ectodomain fragment is:

(SEQ ID NO: 9)
ENSFEMQKGDQNPQIAAHVISEASSKTTSVLQWAEKGYYTMSNNLVTLENG

KQLTVKRQGLYYIYAQVTFCSNREASSQAPFIASLCLKSPGRFERILLRAA

NTHSSAKPCGQQSIHLGGVFELQPGASVFVNVTDPSQVSHGTGFTSFGLLK

L.

Another exemplary CD40L ectodomain fragment is:

(SEQ ID NO: 10)
MQKGDQNPQIAAHVISEASSKTTSVLQWAEKGYYTMSNNLVTLENGKQLTV

KRQGLYYIYAQVTFCSNREASSQAPFIASLCLKSPGRFERILLRAANTHSS

AKPCGQQSIHLGGVFELQPGASVFVNVTDPSQVSHGTGFTSFGLLKL.

In some embodiments, the agonist for CD40 comprises the ectodomain of the human CD40L. In other embodiments, the agonist for CD40 comprises a fragment of the CD40L comprising at least 20, 30, 40, 50, 60, 70, 80, 90, 100, 110, 120, 130, 140, 150, 160, 170, 180, 190, 200, 210, 220, 230, 240, 250, 260, 270 or 279 contiguous amino acids of the full-length CD40L protein, wherein the fragment binds to and triggers CD40.

Configuration of Fusion Protein

In the fusion protein of the present invention, when prepared by recombinant methods described elsewhere herein, the coding sequences of the two components are fused together in frame, either directly or through a linker. As used herein, the term "directly" refers to a fusion of the two components without a peptide linker in between (i.e., in an expression construct, the codons encoding Component A are contiguous with the codons encoding Component B). As used herein, "fused in frame" means that the expression of the fused coding sequences results in the fusion protein comprising both the first and the second polypeptides. Accordingly, there is no translational terminator between the reading frames of the two components.

Configuration A-B

In one aspect of the invention, the N-terminus of Component B is fused to the C-terminus of Component A, either directly or indirectly via a peptide linker, resulting in $NH_3$-A-{optional linker}-B—COOH configuration. See FIG. 1A. In any of the herein embodiments, a linker peptide may optionally be present between Components A and B. In embodiments including an scFv, the variable domains may be arranged, N-terminal to C-terminal, either as $V_H$-$V_L$ or as $V_L$-$V_H$. In embodiments of the invention where the agonist for OX40 and/or CD40 is derived from a monoclonal antibody, the monoclonal antibody is preferably fully human. If not fully human, it is preferable that the framework sequence (between the CDRs of the variable regions) be human, e.g., a humanized antibody. Where the agonist is a $V_HC_H$, it is preferred that at least the $C_H$ domain is human, e.g., a chimeric antibody. The $V_H$ domain of the $V_HC_H$ may also be humanized.

In one aspect, the fusion protein comprises an OX40 agonist derived from an agonist monoclonal antibody fused to a CD40 agonist. In some embodiments, the OX40 agonist is selected from the group consisting of scFvOX40, $V_HC_H$OX40, and $V_H$HOX40.

In one embodiment, the fusion protein comprises scFvOX40 fused to the ectodomain of CD40L. See FIG. 1B. In one embodiment, the scFvOX40 comprises the $V_H$ and $V_L$ chains of an agonist monoclonal antibody against human OX40, and the ectodomain of CD40L comprises SEQ ID NO: 10.

In another embodiment, the fusion protein comprises $V_HC_H$OX40 fused to the ectodomain of CD40L. See FIG. 1C. In one embodiment, $V_HC_H$OX40 comprises the $V_H$ and constant region of the heavy chain of an agonist monoclonal antibody against human OX40, and the ectodomain of CD40L comprises SEQ ID NO: 10.

In another embodiment, the fusion protein comprises scFvOX40 or V$_H$C$_H$OX40 as Component A fused to scFvCD40 or V$_H$C$_H$CD40 as Component B. See FIG. 1D. In one embodiment of the fusion protein, scFvOX40 is fused to scFvCD40 or to V$_H$C$_H$CD40. In another embodiment, V$_H$C$_H$OX40 is fused to scFvCD40 or V$_H$C$_H$CD40. These embodiments typically include a linker between Components A and B to enable proper folding of the two components and minimize steric problems.

In another aspect, the fusion protein comprises the ectodomain of OX40L as Component A. In an embodiment, the fusion protein comprises the ectodomain of OX40L, or functional fragment thereof, as Component A, fused directly or indirectly via a peptide linker to the ectodomain of CD40L, or a functional fragment thereof as Component B. See FIG. 1E. In one embodiment, the OX40L ectodomain is from human OX40L and the CD40L ectodomain is from human CD40L. In an embodiment, Component A comprises: SEQ ID NO: 2 and Component B comprises SEQ ID NO: 10.

Configuration B-A

In another aspect of the invention, the N-terminus of Component A is fused to the C-terminus of Component B, either directly or indirectly via a peptide linker, resulting in NH$_3$—B-{optional linker}-COOH configuration. See FIG. 2A. In any of the embodiments, a linker peptide may optionally be present between Components A and B.

In one aspect, the fusion protein comprises a CD40 agonist derived from an agonist monoclonal antibody fused to an OX40 agonist. In some embodiments, the CD40 agonist is selected from the group consisting of scFvCD40, V$_H$C$_H$CD40, and V$_H$HCD40.

In one embodiment, the fusion comprises scFvCD40 fused to the ectodomain of OX40L. See FIG. 2B. In one embodiment, the scFvCD40 comprises the V$_H$ and V$_L$ chains of antibody an agonist monoclonal antibody against human CD40 and the ectodomain of OX40L comprises SEQ ID NO: 2.

In a preferred embodiment, the fusion protein of the invention comprises scFvCD40 fused to the ectodomain of OX40L comprising SEQ ID NO: 2, and further comprising a linker between Components B and A. In an embodiment, the fusion protein of the invention comprises scFvCD40 fused to the ectodomain of OX40L and further comprising a linker between Components B and A. In an embodiment, the linker is the hinge region of human IgG1 (EPKSCDK-THTCPPCP; SEQ ID NO: 11); the C$_{H2}$ and C$_{H3}$ domains of aglycosylated human IgG1; and a second IgG1 hinge region (SEQ ID NO: 11). In this embodiment, the ectodomain of OX40L may comprise SEQ ID NO. 2.

In another embodiment, the fusion protein comprises V$_H$C$_H$CD40 fused to the ectodomain of OX40L. See FIG. 2C. In one embodiment, V$_H$C$_H$CD40 comprises the V$_H$ and constant region of the heavy chain of an agonist monoclonal antibody against human CD40 and the ectodomain of OX40L comprises SEQ ID NO: 2).

In a preferred embodiment, the fusion protein of the invention comprises V$_H$C$_H$CD40 fused to the ectodomain of OX40L comprising SEQ ID NO: 2, and further comprising a linker between Components B and A. In an embodiment, the fusion protein of the invention comprises V$_H$C$_H$CD40 fused to the ectodomain of OX40L and further comprising a linker between Components B and A. In an embodiment, the linker is the hinge region of human IgG1 (EPKSCDK-THTCPPCP; SEQ ID NO: 11); the C$_{H2}$ and C$_{H3}$ domains of aglycosylated human IgG1; and a second IgG1 hinge region (SEQ ID NO: 11). In this embodiment, the ectodomain of OX40L may comprise SEQ ID NO: 2).

In another embodiment, the fusion protein comprises scFvCD40 or V$_H$C$_H$CD40 as Component B fused to scFvOX40 or V$_H$C$_H$OX40 as Component A. See FIG. 2D. In one embodiment of the fusion protein, scFvCD40 is fused to scFvOC40 or to V$_H$C$_H$OX40. In another embodiment, V$_H$C$_H$CD40 is fused to scFvOC40 or V$_H$C$_H$OX40. These embodiments typically include a linker between Components A and B to enable proper folding of the two components and minimize steric problems.

In another aspect, the fusion protein comprises the ectodomain of CD40L as Component B. In an embodiment, the fusion protein comprises the ectodomain of CD40L, or functional fragment thereof, as Component B, fused directly or indirectly via a peptide linker to the ectodomain of OX40L, or a functional fragment thereof as Component A. In one embodiment, and the CD40L ectodomain is from human CD40L and the OX40L ectodomain is from human OX40L. In an embodiment, Component B comprises SEQ ID NO: 10, and Component A comprises SEQ ID NO: 2.

Linkers

In some embodiments, the components of the fusion protein of the invention may be optionally connected via a peptide linker. The residues for the linker may be selected from naturally occurring amino acids, non-naturally occurring amino acids, and modified amino acids. The linker will typically connect the carboxy terminus of the first component to the amino terminus of the second component. The linker may alter the distance between the two structural components of the fusion protein, as well as alter the flexibility of this region. The linker may comprise any number of amino acids. The linker may thus comprise, for example, 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. In some embodiments, the linker may be composed of from 3 to 60 amino acid residues, from 3 to 40 amino acids, from 3 to 30 amino acids, from 3 to 24 amino acids, from 3 to 18 amino acids, or from 3 to 15 amino acids. The linker may comprise, for example, a repeating sub-sequence of 2, 3, 4, 5 or more amino acid residues, comprising 2, 3, 4, 5, 6, 7, 8, 9, 10, 11, 12 or more repeats of the sub-sequence.

Linkers may be naturally-occurring sequences or designed sequences. Peptide linkers useful in the molecule of the invention include, but are not limited to, glycine linkers, glycine-rich linkers, serine-glycine linkers, and the like. A glycine-rich linker comprises at least about 50% glycine and preferably at least about 60% glycine. In one embodiment, the linker comprises the amino acid sequence Gly-Ser, or repeats thereof. See, e.g., Huston, et al., *Methods in Enzymology*, 203:46-88 (1991). In another embodiment, the linker comprises the amino acid sequence Glu-Lys, or repeats thereof. See, e.g., Whitlow et al., *Protein Eng.*, 6:989 (1993)). In another embodiment, the linker comprises the amino acid sequence Gly-Gly-Ser, or repeats thereof. In another embodiment, the linker comprises the amino acid sequence Gly-Gly-Gly-Gly-Ser (SEQ ID NO: 12), or repeats thereof. In certain specific embodiments, the linker contains from 2 to 12 repeats of Gly-Gly-Ser or Gly-Gly-Gly-Gly-Ser (SEQ ID NO: 13). See U.S. Pat. No. 6,541,219 for examples of peptide linkers. In one embodiment, the linker may comprise the sequence: GDPLVTAASVLEF-GGSGGGSEGGGSEGGGSEGGGSDI (SEQ ID NO: 14).

Linkers comprising human immunoglobulin Fc region sequences are also useful. An exemplary Fc region linker includes but is not limited to: the hinge region of human IgG1 (EPKSCDKTHTCPPCP; SEQ ID NO: 11); the $C_{H2}$ and $C_{H3}$ domains of a human IgG1; and a second IgG1 hinge region. An exemplary sequence for this linker comprises the following sequence, wherein the hinge region sequences are underlined:

```
                                       (SEQ ID NO: 15)
EPKSCDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GKEPKSCDKT

HTCPPCP
```

In another embodiment, the hinge region and the $C_{H2}$ and $C_{H3}$ domains of human IgG1 are mutated to prevent inter-chain disulfide bonds, to reduce antibody dependent cellular cytotoxicity (ADCC), or to eliminate N-linked glycosylation (aglycosylated human IgG1). An exemplary sequence for this linker comprises the sequence below, wherein mutated sequences are in bold and underlined.

```
                                       (SEQ ID NO: 16)
EPKSSDKTHT SPPSPAPPVA GAPSVFLFPP KPKDTLMISR

TPEVTCVVVD VSHEDPEVKF NWYVDGVEVH NAKTKPREEQ

YASTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GK
```

Linkers are useful for separating the two components of the fusion protein to enable proper folding of the components, to reduce potential steric problems, and/or to contribute optimal receptor binding. The skilled artisan is familiar with the design and selection of peptide linkers. See, for instance, Robinson et al., 1998, *Proc. Natl. Acad. Sci. USA* 95:5929-5934. Automated programs are also available for peptide linker design (e.g., Crasto et al., 2000, *Protein Engineering* 13:309-312).

Optional Other Elements

The fusion protein optionally may also include further elements apart from Component A, Component B and the optional linker. Such further elements may include: an initiator methionine, a signal peptide, an antigen polypeptide, and a purification tag, such as His-6. Fusion proteins essentially consisting of Component A and Component B and an optional linker are preferred embodiments in the context of the present invention.

Fusion proteins of the invention optionally comprise a signal peptide. Signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

Activity

In one embodiment, the fusion proteins of the present invention stimulate the immune system by stimulating antigen-present cells (APCs) and local activated T cells. In some embodiments, the fusion protein of the invention increases pro-inflammatory cytokines and chemokines, such as IL-2, IL-4 and IFN-gamma. The activity of the fusion protein of the invention and the methods of using the fusion protein embrace up-regulation of any and all cytokines that are either promoted by OX40 ligand binding to OX40 and/or by the CD40 ligand binding to CD40.

In other embodiments, the fusion proteins of the present invention promote tumor cell death, promote death of virally-infected cells, and reduce cell death of monocytes.

Most (although not all) of the TNF receptor (TNFR) superfamily members are type II transmembrane proteins. These proteins contain an extracellular domain that is structurally characterized by the presence of one to six cysteine-rich domains (CRDs). The typical CRD is approximately 40 amino acids in length and contains six conserved cysteine residues that form three intra-chain disulphide bridges. The CRD itself is typically composed of two distinct structural modules.

OX40L

OX40L is a Type II membrane protein having 183 amino acids and has been sequenced in a number of species, including, but not limited to, mouse: GENBANK® Accession no. NP_033478.1; Human: GENBANK® Accession no. NP_003317.1; *Rattus norvegicus*: GENBANK® Accession no. NP_446004.1; *Sus Scrofa* (pig): GENBANK® Accession no. NP_001020388.1; *Macaca mulatta* (rhesus monkey): GENBANK® Accession no. XP_001101190.1; *Callithrix jacchus* (New World Monkey): GENBANK® Accession no. XP_002760448.1; and *Oryctolagus cuniculus* (rabbit): GENBANK® Accession no. NP_001075454.1.

The extracellular domain of human OX40L comprises about amino acids 47 to 183 (underlined) in the following sequence:

```
                                       (SEQ ID NO: 17)
MERVQPLEENVGNAARPRFERNKLLLVASVIQGLGLLLCFTYICLHFSALQ

VSHRYPRIQSIKVQFTEYKKEKGFILTSQKEDEIMKVQNNSVIINCDGFYL

ISLKGYFSQEVNISLHYQKDEEPLFQLKKVRSVNSLMVASLTYKDKVYLNV

TTDNTSLDDFHVNGGELILIHQNPGEFCVL.
```

TNF ligands share a common structural motif, the TNF homology domain (THD), which binds to the cysteine-rich domains (CRDs) of TNF receptors. The TNF domain of OX40L responsible for receptor binding is amino acids 57-183 (bolded in SEQ ID NO: 17), based on TNF homology models. The extracellular domain trimerizes to form a homotrimer.

CD40L

CD40L is a Type II membrane protein having 261 amino acids and has been sequenced in a number of species, including, but not limited to, mouse: GENBANK® Accession no. NP_035746.2; human: GENBANK® Accession no. NP_000065.1; *Rattus norvegicus*: GENBANK® Accession no. NP_445805.1; *Callithrix jacchus* (white-tufted-ear marmoset): GENBANK® Accession no. NP_001254684.1; *Felis catus* (domestic cat): GENBANK® Accession no. NP_001009298.1; *Gallus gallus* (chicken): GENBANK® Accession no. NP_990064.1; *Sus scrofa* (pig): GENBANK® Accession no. NP_999291.1; *Macaca mulatta* (Rhesus monkey: GENBANK® Accession no.

NP_001028011.1; *Canis lupus familiaris* (dog): GEN-BANK® Accession no. NP_001002981.1; *Bos taurus* (Cattle): GENBANK® Accession no. NP_777049.1; and *Danio rerio* (zebrafish): GENBANK® Accession no. NP_001138281.1.

The extracellular domain of human CD40L comprises about amino acids 45 to 261 (underlined) in the following sequence:

(SEQ ID NO: 18)
MIETYNQTSPRSAATGLPISMKIFMYLLTVFLITQMIGSALFAVYLHRRLD

KIEDERNLHEDFVFMKTIQRCNTGERSLSLLNCEEIKSQFEGFVKDIMLNK

EETKKENSFEMQKGDQNPQIAAHVISEASSKTTSVLQWAEKGYYTMSNNLV

TLENGKQLTVKRQGLYYIYAQVTFCSNREASSQAPFIASLCLKSPGRFERI

LLRAANTHSSAKPCGQQSHILGGVFELQPGASVFVNVTDPSQVSHGTGFTS

FGLLKL.

The TNF homology domain responsible for receptor binding is amino acids 122 to 259 (bolded in SEQ ID NO: 18), based on TNF homology models. The extracellular domain of CD40L also trimerizes to form a homotrimer.

Modification

This invention relates to a fusion protein comprising an agonist of OX40 and an agonist of CD40. The invention also encompasses variants of the fusion proteins. While in general it is desirable for variants to show enhanced ability for binding to a given molecule, in some embodiments variants may be designed with slightly reduced activity as compared to other fusion proteins of the invention, for example, in instances in which one would purposefully want to attenuate activity. Furthermore, variants or derivatives can be generated that would have altered multimerization properties. When engineering variants of OX40L, this may be done for either the entire OX40L ectodomain, or for that component of the ectodomain that is incorporated within the fusion protein itself. Similarly, engineering variants of CD40L may be done for either the entire CD40L ectodomain, or for that component of the ectodomain that is incorporated within the fusion protein itself.

Preferably, variants or derivatives of the fusion proteins of the present invention maintain the hydrophobicity/hydrophilicity of the amino acid sequence.

The invention also provides chemical modification of a fusion protein of the invention. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention. Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylation site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis (Gillman et al., *Gene* 8:81 (1979); Roberts et al., *Nature* 328:731 (1987) or Innis (Ed.), 1990, *PCR Protocols: A Guide to Methods and Applications*, Academic Press, New York, N.Y.) or the polymerase chain reaction method (PCR; Saiki et al., *Science* 239:487 (1988)), as exemplified by Daugherty et al. (*Nucleic Acids Res.* 19:2471 (1991)) to modify nucleic acids encoding the complete receptors.

Additional modifications can be introduced such as those that further stabilize the OX40L trimer and/or the CD40L trimer and/or increase affinity of binding to OX40 or CD40 respectively. As discussed elsewhere herein, spacers/linkers can be added to alter the distance between the two structural components of the fusion protein, as well as alter the flexibility of this region.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath, 1992, *Protein Expr Purif* 3-0.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and the fusion of Components A and B is useful to facilitate purification.

Expression of Fusion Proteins

The amino acid sequences of the present invention may be produced by expression of a nucleotide sequence coding for same in a suitable expression system.

Fusion expression vectors include pGEX (Pharmacia, Piscataway, N.J.), pMAL™ (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

As discussed above, a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion protein of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

The amino acid sequences of the present invention may be produced by expression of a nucleotide sequence coding for same in a suitable expression system.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) *Proteins: Structures And Molecular Principles*, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for Fusion Protein Activity

Any of the various immunologic assays known in the art may be used to measure the immunologic activity of any fusion protein.

For example, any one of several conventional assays for monitoring cytokine production, as a measure of immune cells activation and differentiation, can be invoked. For example, for tracking T cell activation, interleukin-2 can be employed as a marker, which can be assayed as described in Thompson et al. (1989, *Proc. Natl. Acad. Sci. USA.* 86:1333) the entire disclosure of which is incorporated herein by reference. A kit for an assay for the production of interferon is also available from Genzyme Corporation (Cambridge, Mass.). One can also employ immunofluorescence and flow cytometry to monitor cytokine production on a cellular basis, and to monitor cell surface markers that reflect cellular activation and/or differentiation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of 3H-labeled thymidine incorporated into the replicating DNA of cultured cells. Therefore, the rate of DNA synthesis and, in turn, the rate of cell division can be quantified.

Another assay for monitoring T cell proliferation is based on loading T cells with the CFSE dye, and subsequently monitoring by flow cytometry the dilution of this dye that accompanies successive cell divisions. In addition to monitoring the stimulation of T cell proliferation, the bioactivity of the fusion protein can also be monitored by evaluating its capacity to induce maturation of antigen-presenting cells. By combining APCs expressing CD40 on their surface with T cells expressing OX40 on their surface, one can assess whether a fusion protein or derivative thereof triggers signaling of CD40 and enhances T cell proliferation. In the setting of tumor cells, one can assess whether a fusion protein or derivative triggers CD40-induced cell death in the tumor cells and locally enhances T cell proliferation and effector T cell function, and reduces regulatory T cell activity.

Utility and Treatment Methods

The fusion protein of the invention advantageously provides dual-signaling capability within a single cell expressing both OX40 and CD40. The dual-signaling capacity is also efficacious in bridging CD40-expressing cells and OX40-expressing cells. The dual-signaling capacity thus offers increased efficacy over, for instance, individual receptor triggering by CD40L:Fc fusion protein. In addition, the fusion protein of the invention offers increased signaling from co-localization (clustering) of receptors. The fusion protein of the invention also provided enhanced specificity for cells expressing both CD40 and OX40 receptors, and functional synergies may be achieve by co-triggering receptors. Enhanced specificity may lead to lower doses for achieving comparable efficacy relative to prior art individual receptor triggering fusion proteins, such as CD40L-Fc. It is also contemplated that the enhanced specificity may lead to reduced dosing frequency needed for achieving comparable efficacy, relative to prior art individual receptor triggering fusion proteins. Reduction in dosing and/or dosing frequency advantageously may reduce undesirable side effects that can arise in individual receptor triggering fusions, such as CD40L:Fc.

The fusion protein of the invention has at least three modes of action for therapeutic effect. The following description of modes of action is not intended to be limiting and should not be construed that way. In addition, the modes are not intended to be mutually exclusive.

In one mode, Component A of the fusion protein binds and triggers CD40 on an antigen-presenting cell, such as a dendritic cell, and Component B binds and triggers OX40 expressed on an activated T cell. Triggering of CD40 on the APC results in biological signaling that promotes maturation of the dendritic cell and also promotes the T-cell stimulatory capacity of the dendritic cell. Triggering of OX40 on an activated T cell augments clonal expansion and survival of the T cell. OX40 signaling may also augment effector T cell differentiation and development of memory response. Coupling CD40 signaling in an APC with OX40 signaling in a local activated T cell therefore enhances immune response in the immediate term and the long term. Accordingly, the mode is an immunostimulatory mode.

The fusion protein of the invention accordingly may be used in therapeutic methods that would benefit from its immuno-potentiation activity. In one embodiment, the fusion protein is used as an adjuvant for a vaccine. Exemplary vaccines for this embodiment include, but are not limited to, a malaria vaccine, a tuberculosis vaccine, and a cancer vaccine. In one embodiment, the fusion protein of the invention may be part of the vaccine formulation. In another embodiment, the fusion protein is administered separately from the vaccine. The vaccine may be prophylactic or therapeutic.

In another embodiment, the fusion protein of the invention is incorporated into a treatment regimen that includes administration of genetically altered T cells to a subject. This treatment regimen is applicable to HIV infection and cancer, as well as a broad range of other disease. See, for instance, Scholler et al., (2012, "Decade-Long Safety and Function of Retroviral-Modified Chimeric Antigen Receptor T Cells," *Sci Transl Med*, 2 May 2012 4:132ra53 DOI: 10.1126/scitranslmed.3003761.) The fusion protein is administered with, before or after, administration of genetically altered T cells to a subject to stimulate the immune response of the T cells in the subject. In another embodiment, the genetically altered T cells are further genetically altered to express and secrete the fusion protein of the present invention.

In another mode, Component B binds and triggers CD40 expressed on tumor cells and Component A binds and triggers OX40 expressed on tumor-infiltrating T cells. Binding and triggering of CD40 on the tumor cell can lead to tumor cell death. Additionally, tumor-infiltrating T cells include both regulatory T cells and effector T cells. However, tumor-infiltrating regulatory T cells interfere with the anti-tumor effector T-cell immunity within tumor beds. OX40 binding on regulatory T cells advantageously inhibits the suppressive activity of the regulatory T cells, while OX40 binding on effector T cells stimulates their activity. As a result, tumor-directed cytotoxic T cells are stimulated in their tumor-directed cytotoxic activity.

CD40 is expressed on a wide range of tumor cells, including but not limited to, non-Hodgkin's lymphoma, Hodgkin's lymphomas, multiple myeloma, and carcinomas, such as nasopharynx, bladder, cervix, kidney and ovary. Thus, in one embodiment, the invention provides a method of treating a proliferative disorder by administering a therapeutically effective amount of a fusion protein of the invention to a subject diagnosed with a proliferative disorder.

The fusion proteins according to the invention may be administered to individuals (such as mammals, including animals and humans) afflicted with a cellular proliferative disorder such as cancer, and malignant and benign tumors. In a particular embodiment of the invention, the individual treated is a human.

The fusion proteins are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

In one embodiment of the method of treatment of a proliferative disorder, the proliferative disorder is a hematological B cell malignancy. In one embodiment, the B cell malignancy is B cell lymphoma. In another embodiment, the proliferative disorder is melanoma.

Another therapeutic target for the fusion protein of the invention are persistent viral infections. For instance, there is evidence that dysregulation of CD40L in CD4+ T cells in HIV-1 infections contributes to immunodeficiency because of a decrease in dendritic cell maturation. Administering the fusion protein of the invention may mitigate the effect of the dysregulation of CD40L in the CD4+ T cells, while also triggering OX40 in local activated T cells. In addition, anti-viral T cells, including cytotoxic T cells, express high levels of OX40. Cytotoxic T cells can destroy virally-infected cells. Binding OX40 on anti-viral T cells may lead to a sustained anti-viral immune response.

Thus, the invention also provides a method of treating a persistent viral infection by administering a therapeutically effective amount of a fusion protein of the invention to a subject diagnosed with a persistent viral infection. In one embodiment, the viral infection is chronic hepatitis. In one embodiment, the viral infection is herpes virus-induced disease. In one embodiment, the persistent viral infection is HIV/AIDS (Human immunodeficiency virus infection/acquired immunodeficiency syndrome).

In another mode, the fusion protein of the invention competes with CD40L-expressing monocytes for binding to CD40 receptors on tumor cells. Monocytes exhibit significant cytotoxic activity against tumor cells. However, when the CD40L of CD40L-expressing monocytes binds to CD40 on tumor cells, the monocytes are activated, which leads to cell death of the monocyte. Thus, CD40 plays a role in tumor cells' evasion of monocyte cytotoxic activity. The competition for binding to CD40 on tumor cells by the fusion protein of the invention leads to a diminution of the cell death of activated monocytes, preserving their cytotoxic activity against tumor cells. Accordingly, this mode of action for the fusion protein of the invention is also expected to contribute to the fusion protein's its efficacy as an anti-proliferative disorder therapeutic.

Pharmaceutical Compositions and Dosing Regimens

Administration of the compositions of the invention is typically parenteral, by subcutaneous, intravenous, intramuscular, or intraperitoneal injection, or by infusion or by any other acceptable systemic method. In a preferred embodiment, administration is by subcutaneous injection. In another preferred embodiment, administration is by intravenous infusion, which may typically take place over a time course of about 1 to 5 hours. In addition, there are a variety of oral delivery methods for administration of therapeutic proteins, and these can be applied to the therapeutic fusion proteins of this invention.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight. Various modifications or derivatives of the fusion proteins, such as addition of polyethylene glycol chains (PEGylation), may be made to influence their pharmacokinetic and/or pharmacodynamic properties.

To administer the fusion protein by other than parenteral administration, it may be necessary to coat the protein with, or co-administer the protein with, a material to prevent its inactivation. For example, protein may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., 1984, *J. Neuroimmunol.* 7:27).

Although the compositions of the invention can be administered in simple solution, they are more typically used in combination with other materials such as carriers, preferably pharmaceutically acceptable carriers. Useful pharmaceutically acceptable carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g., *Remington's Pharmaceutical Science*, 17th Ed. (Mack Publishing Company, Easton, Pa., 1990). Alternatively, compositions of the invention may be introduced into a patient's body by implantable drug delivery systems (Urquhart et al., 1984, *Ann. Rev. Pharmacol. Toxicol.* 24:199).

Therapeutic formulations may be administered in many conventional dosage formulations. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications*, Dekker, N.Y.; Lieberman et al. (eds.) (1990) *Pharmaceutical Dosage Forms: Tablets*, Dekker, N.Y.; and Lieberman et al. (eds.) (1990), *Pharmaceutical Dosage Forms: Disperse Systems*, Dekker, N.Y.

In additional embodiments, the present invention contemplates administration of the fusion proteins by gene therapy methods, e.g., administration of an isolated nucleic acid encoding a fusion protein of interest. The protein building blocks (e.g., Component A and Component B) of the fusion protein of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, is also well within the ability of one skilled in the art. Administration of an isolated nucleic acid encoding the fusion protein is encompassed by the expression "administering a therapeutically effective amount of a fusion protein."

Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., 1998, *Circulation* 97:

12, 1114-1123, and more recently, Fatham, 2007, "A gene therapy approach to treatment of autoimmune diseases," *Immun. Res.* 18:15-26; and U.S. Pat. No. 7,378,089, both incorporated herein by reference. See also Bainbridge et al., 2008, "Effect of gene therapy on visual function in Leber's congenital Amaurosis,"*N Engl Med* 358:2231-2239; and Maguire et al., 2008, "Safety and efficacy of gene transfer for Leber's congenital Amaurosis,"*N Engl J Med* 358:2240-8. There are two major approaches for introducing a nucleic acid encoding the fusion protein (optionally contained in a vector) into a patients cells; in vivo and ex vivo. For in vivo delivery, the nucleic acid is injected directly into the patient, usually at the site where the fusion protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes simplex I virus, adeno-associated virus), lipid-based systems (useful lipids for lipid-mediated transfer of the gene are DOTMA, DOPE and DC-Chol, for example); naked DNA; and transposon-based expression systems. For review of gene marking and gene therapy protocols, see Anderson et al., (1992) *Science* 256:808-813. See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. Fusion proteins of the present invention can be delivered using gene therapy methods, for example locally in tumor beds, intrathecally, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the fusion proteins of the present invention, and then returning the transfected cells to the individual's body.

The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

The example below is described with respect to a representative agonist fusion protein for CD40 and OX40, an scFvCD40 fused to the ectodomain of OX40L by way of a linker. However, a person of skill in the art would understand how to conduct the corresponding experiments with any other embodiment of the fusion protein of the invention.

EXAMPLES

Example 1

Agonist Fusion Protein for CD40 and OX40

A novel fusion protein comprising an scFvCD40 fused to the ectodomain of OX40L via an intervening peptide linker is prepared. The scFvCD40 comprises the variable regions from the light and heavy chains of G28-5 (mouse monoclonal anti-human CD antibody; commercially available from BioLegends®); SEQ ID NO: 4 and SEQ ID NO: 5, respectively. The ectodomain of OX40L has the sequence SEQ ID NO: 2. The linker is SEQ ID NO: 15.

The chimeric coding sequence for this fusion protein is subcloned into the eukaryotic expression vector pMFneo. In turn, the resulting expression construct is stably transfected into HEK 293 cells. The fusion protein is detected in conditioned media from the transfectants, with the expected sizes verified on western blots of reducing denaturing gels using an anti-human OX40L antibody (Abcam, Cambridge, Mass.).

A high-yield, multi-step chromatographic purification may be used for the isolation of highly-purified scFvCD40-OX40L protein. The process includes an efficient capture step, an anion-exchange chromatography step, and then a final buffer exchange step, the latter carrying the product into the formulation buffer. A seven-liter production fermentation followed by the above purification process, yields purified scFvCD40-OX40L, which may be used for in vitro and in vivo experiments, such as those indicated below.

To validate the identity of the scFvCD40-OX40L protein, its ability to bind CD40 and OX40 is assessed. To detect binding to CD40, a human B cell line lacking OX40 expression (e.g., Daudi cells) is incubated with purified scFvCD40-OX40L protein. The cells are immunostained with a PE-anti-human OX40L mAb and analyzed by flow cytometry. To detect binding to OX40, CHO cells are transiently transfected with a human OX40 cDNA expression construct, and after 48 hours, transfectants are incubated with purified scFvCD40-OX40L protein. The cells are immunostained with a PE-anti-human IgG1 mAb (Fcg-specific) and analyzed by flow cytometry.

To assess the functionality of the scFvCD40 component of the scFvCD40-OX40L fusion protein, the capacity of the fusion protein to stimulate proliferation of human B cells isolated from peripheral blood is assessed. The B cells may be isolated using a B cell separation kit (StemCell Technologies). Purified scFvCD40-OX40L is incubated for 72 h at 37° C. with human B cells, adding $^3$H-thymidine for the final 18 hours. Cells are harvested and counted in a beta counter (Wallac®). To assess the functionality of the OX40L component of the scFvCD40-OX40L fusion protein, the ability of the fusion protein to co-stimulate IL-2 production in a T cell line is assessed. Purified scFvCD40-OX40L will be incubated for 24 h at 37° C. with Hut102 cells, an HTLV-I infected T cell line expressing OX40 receptor, and the culture supernatant is analyzed for IL-2 levels using a human IL-2 ELISA kit (eBioscience). Alternative, co-stimulatory activity is measured by using purified human CD4+ T cells, and stimulating proliferation with a combination of anti-CD3 mAb and scFvCD40-OX40L fusion protein. For all functional assays, the activity of scFvCD40-OX40L fusion protein is compared to its component parts (scFvCD40-hFc and hFc-OX40L) or anti-human CD40 and anti-human OX40 mAb, added to culture individually or combined together. This comparison allows for an assessment of the fusion protein compared to its component parts.

To permit in vivo expression, the same coding sequences is ligated into the expression cassette of pND, downstream of the CMV promoter.

Whereas particular embodiments of this invention have been described above for purposes of illustration, it will be evident to those skilled in the art that numerous variations of the details of the present invention may be made without departing from the invention as defined in the appended claims.

The disclosures of each and every patent, patent application, publication, GENBANK®, UniProtKB, or SwissProt record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. An OX40L/scFvCD40 antibody fusion protein comprising an OX40L comprising the amino acid sequence of SEQ ID NO: 2 and a scFvCD40 antibody comprising the amino acid sequence of SEQ ID NO: 4 and the amino acid sequence of SEQ ID NO: 5, and further comprising a linker between said OX40L and said scFvCD40 antibody, wherein the linker comprises the amino acid sequence of SEQ ID NO: 14 or SEQ ID NO: 16.

2. A pharmaceutical composition comprising a pharmaceutically acceptable carrier and the fusion protein of claim 1.

3. A method of stimulating the immune system of a patient comprising administering a therapeutically effective amount of the fusion protein of claim 1 to a patient in need of such treatment.

4. The method of claim 3, further comprising administering a vaccine to the patient.

5. The method of claim 4, wherein the fusion protein and the vaccine are administered simultaneously.

6. The method of claim 4, wherein the fusion protein and the vaccine are administered sequentially.

7. A method for stimulating the immune system of a patient in need thereof, comprising administering a therapeutically effective amount of the composition of claim 2 to the patient.

8. The method of claim 3, wherein the patient has a proliferative disorder.

9. The method of claim 8, wherein the proliferative disorder is cancer.

10. The method of claim 9, wherein the cancer is a hematological B cell malignancy or melanoma.

11. The method of claim 7, wherein the patient has a proliferative disorder.

12. The method of claim 11, wherein the proliferative disorder is cancer.

13. The method of claim 12, wherein the cancer is a hematological B cell malignancy or melanoma.

* * * * *